(12) United States Patent
Coles, Jr.

(10) Patent No.: US 8,445,034 B1
(45) Date of Patent: May 21, 2013

(54) SYSTEMS AND METHODS FOR PRODUCING ORGANIC CANNABIS TINCTURE

(76) Inventor: Albert L Coles, Jr., Stinson Beach, CA (US)

( * ) Notice: Subject to any disclaimer, the term of this patent is extended or adjusted under 35 U.S.C. 154(b) by 0 days.

(21) Appl. No.: 13/283,550

(22) Filed: Oct. 27, 2011

Related U.S. Application Data (60) Provisional application No. 61/409,464, filed on Nov. 2, 2010.

(51) Int. Cl.
*A01N 65/00* (2009.01)

(52) U.S. Cl.
USPC .................................................. 424/725

(58) Field of Classification Search
None
See application file for complete search history.

(56) References Cited

U.S. PATENT DOCUMENTS

| | | | |
|---|---|---|---|
| 6,730,330 B2 | 5/2004 | Whittle et al. |
| 6,946,150 B2 | 9/2005 | Whittle |
| 7,025,992 B2 | 4/2006 | Whittle et al. |
| 7,344,736 B2 | 3/2008 | Whittle et al. |
| 7,622,140 B2 | 11/2009 | Whittle et al. |
| 7,674,922 B2 | 3/2010 | Burdick et al. |
| 7,700,368 B2 | 4/2010 | Flockhart et al. |
| 7,709,536 B2 | 5/2010 | Whittle |
| 7,968,594 B2 | 6/2011 | Guy et al. |
| 8,034,843 B2 | 10/2011 | Whittle et al. |
| 2003/0191180 A1 | 10/2003 | Ross et al. |
| 2004/0049059 A1 | 3/2004 | Mueller |
| 2006/0135599 A1 | 6/2006 | Symonds et al. |
| 2006/0153941 A1 | 7/2006 | Musty et al. |
| 2008/0031977 A1 | 2/2008 | Musty et al. |
| 2008/0119544 A1 | 5/2008 | Guy et al. |
| 2008/0139667 A1 | 6/2008 | Robson et al. |
| 2008/0167483 A1 | 7/2008 | Whittle et al. |
| 2009/0197941 A1 | 8/2009 | Guy et al. |
| 2009/0306221 A1 | 12/2009 | Guy et al. |
| 2010/0016418 A1 | 1/2010 | Guy et al. |
| 2010/0035978 A1 | 2/2010 | Guy et al. |
| 2010/0119606 A1 | 5/2010 | Whittle et al. |
| 2010/0168448 A1 | 7/2010 | Flockhart et al. |
| 2010/0239693 A1 | 9/2010 | Guy et al. |
| 2010/0249223 A1 | 9/2010 | Di Marzo et al. |
| 2010/0286098 A1 | 11/2010 | Robson et al. |
| 2010/0292345 A1 | 11/2010 | Pertwee |
| 2010/0317729 A1 | 12/2010 | Guy et al. |
| 2010/0323038 A1 | 12/2010 | Ross |
| 2011/0038958 A1 | 2/2011 | Kikuchi et al. |
| 2011/0082195 A1 | 4/2011 | Guy et al. |
| 2011/0098348 A1 | 4/2011 | De Meijer |
| 2011/0230548 A1 | 9/2011 | Bot et al. |
| 2011/0256245 A1 | 10/2011 | Rosenblat et al. |

OTHER PUBLICATIONS http://www.blissedibles.com/blog. Miss Bliss on Tinctures Dec. 5, 2011.

*Primary Examiner* — Michael Meller
(74) *Attorney, Agent, or Firm* — Tran & Associates (57) ABSTRACT

Systems and methods are disclosed for fabricating a medicine by preparing a cannabis plant material and classifying the cannabis plant material into an acid, neutral, or analog form; extracting cannabinoids from the cannabis plant material by either a reflux process through evaporating and condensing the cannabis plant material or an ultrasonic extraction process of the cannabis plant material with ultrasonic waves; and infusing the cannabinoids with an alternative emulsion.

8 Claims, 3 Drawing Sheets

SYSTEMS AND METHODS FOR PRODUCING ORGANIC CANNABIS TINCTURE

This application claims priority to Provisional Application Ser. 61/409,464, filed Nov. 2, 2010, the content of which is incorporated by reference.

BACKGROUND

The present invention relates generally to extracts used for medical purposes and more specifically to cannabis-related products and extracts that provide various benefits and advantages to a mammal.

Cannabis products have been consumed in various forms for thousands of years. The first descriptions of the medical uses date from Chinese herbal texts in the first century A.D. Cannabis products were taken orally in an herbal tea concoction and were used for their pain-relieving and sleep-inducing properties.

In contrast, the use of cannabis in India was largely restricted to smoking the leaf or the resin extract (hashish) for its psychoactive properties. In fact, cannabis was also used in Ayurvedic medicine in India. This practice became incorporated into the Indian life and culture.

The use was spread through Arab lands in the Middle Ages before coming into Europe and the Americas. It was either eaten, usually in the hashish form, or the leaves were smoked. The medical benefits were not utilized by the medical practitioners of the time and the major usage was for its psychoactive properties as a recreational drug.

It was not until the middle of the nineteenth century that cannabis-based medicines were introduced into the West. The tinctures were used orally for the treatment of seizures, neuralgia, insomnia, and dysmenorrhea, among other illnesses. The cannabis-based medications were administered through an alcohol-based extract of hemp plants that were lacking in the most pharmacologically active ingredients, especially tetrahydrocannabinol (THC).

During most of the twentieth century there has been little interest in or advance of the medical use of cannabis. It has been legally prohibited in the United States since 1937. Occasionally small amounts of oil extract have been made available to some licensed university researchers for animal studies. One of the prior authors (Stephen Rosenblatt, M. D., Ph.D.) did animal research from 1969 through 1971 on learning and memory in rats, using injectable THC oil. Little to no human research on the medical uses of cannabis has been done in recent years. It is believed that, to the extent not already legalized, full state and federal legalization of cannabis related products is imminent.

United States Patent Application 20110256245 discloses a method for obtaining an extract from a cannabis plant for medical uses. In one embodiment, a method for obtaining an extract from a cannabis plant for medical uses is provided. The method comprises (a) providing cannabis flower trimmings with trichome material, (b) providing clean, cold water to at least cover cannabis the cannabis flower trimmings, (c) agitating the mixture of cannabis flower trimmings and water (d) soaking the cannabis flower trimming in cold water for at least one minute, (e) removing cannabis flower trimmings from the water, (f) removing the trichome material from the water and (g) drying the trichome material to contain no more than 10% total water weight.

There presently exists a need to provide more effective and safer cannabis extracts for various medical uses, extraction methods that provide unique active compounds that are useful to treat pain and various medical conditions. Additionally, presently known extraction procedures add unwanted toxins and solvents, provide relatively low yields of the active compound, and/or do not provide the desired active ingredient(s) for the particular pain related to medical purpose. The present invention overcomes these limitations and provides other related advantages.

SUMMARY

In one aspect, systems and methods are disclosed for fabricating a medicine by preparing a cannabis plant material and classifying the cannabis plant material into an acid, neutral, or analog form; extracting cannabinoids from the cannabis plant material by either a reflux process through evaporating and condensing the cannabis plant material or an ultrasonic extraction process of the cannabis plant material with ultrasonic waves; and infusing the cannabinoids with an alternative emulsion.

In another aspect, systems and methods are disclosed for fabricating a medicine by preparing a cannabis material from a plant; classifying the cannabis material into specified cannabinoids categories (THCA/CDBA, THC/CBD and THCV/CBDV); grinding the cannabis material; heating (before refluxing or using ultrasonic) the ground cannabis material at predetermined temperatures to induce a decarboxylation of THCA into THC, CBDA into CBD, THCVA into THCV and CBDVA into CBDV; selecting a plant material to solvent amounts using a predetermined ratio; extracting in a predetermined materials to solvent amount required to produce a specified THCA/CBDA, THC/CBD and THCV and CBDV amount for use in one or more remedies; classifying the extracted materials into the specified categories; optimizing the extracted materials for increasing or decreasing potency; and infusing the extracted materials with an alternative to alcohol.

In a third aspect, a system to fabricate medication includes a dryer to dry a cannabis plant material; means for classifying the cannabis plant material into an acid, neutral, or analog form; a grinder to grind the cannabis plant material; a processor executing computer readable code to select a plant material to solvent amounts using a predetermined ratio; an extractor coupled to the processor, the extractor selected from a group including a reflux machine for evaporating and condensing the cannabis plant material or an ultrasonic extractor to extract cannabinoids from the cannabis plant material with ultrasonic waves; wherein the processor controls the extractor to extract in a predetermined materials to solvent amount required to produce a specified THCA/CBDA, THC/CBD and THCV and CBDV amount for use in one or more remedies; and wherein the processor controls the extractor to infuse the cannabinoids with an alternative emulsion.

Implementations of the above aspect can include one or more of the following. Medical Cannabis patients can make medicinal tinctures (oral delivery) safely at home. Medical Cannabis patients can benefit from higher potency tinctures provided by the preferred embodiments. The system can provide tinctures that allow titratable dosages. Medicinal Cannabis patients can get tinctures that are potent in the "acid" form (THCA/CBDA), the "neutral" form (THC/CBD), or the "analog." form (THCV/CBDV). The system provides tinctures that deliver different ratios of the "acids" (THCA/CBDA) that allow them to titrate between the primary acid phytocannabinoids (THCA/CBDA). The system's tinctures deliver different ratios of the neutral phytocannabinoids (THC/CBD) that allow them to titrate between the primary neutral phytocannabinoids (THC/CBD). The system can provide tinctures that deliver different ratios of the "analog"

phytocannabinoids (THCV/CBDV) that allow them to titrate between the primary analog phytocannabinoids (THCV/CBDV). The system can provide tinctures that deliver different ratios of the "acids" (THCA/CBDA), the "neutral" THC/CBD and the "analogs" (THCV/CBDV) that allow them to titrate between the acids, the neutrals and the analog phytocannabinoids cannabinoids.

Advantages of the preferred embodiments may include one or more of the following. Medical Cannabis patients can avoid toxic materials and harmful bi-products in the tinctures they use. This process is organic. It utilizes home bases extractors (reflux, ultrasonic etc.) currently on the market and 190 proof alcohols as a solvent. It produces potent tinctures of the acids, the neutrals and the analog phytocannabinoids in doses that allow medical cannabis patients to titrate their medicine. In contrast to conventional methods for making extracts use complex extraction equipment (Co2), synthetic materials, complex chemicals, or toxic gases such as Petroleum ether, Sulfuric acid, Isopropyl Alcohol, Methanol, Butane, Co2, nitrogen or other gases to extract, the process a. does not use carbon dioxide ($CO_2$)
b. uses all three types of cannabinoids (acid, neutral, and analog).
c. creates doses that are easily used for self-titration for medical patients.
d. does not remove Delta 1 tetrahydro-cannabinol-THC
e. does not concentrate by extracting 100% of the solvent
f. does not use chromatographic fractioning The process uses all Cannabis varieties: Sativa (high THCA/low CBDA), Indica (medium THC/medium CBD, and high THCV and high CBDV) and Ruderalis (low THCA/high CBDA). The resulting products using conventional tincture processes are much lower in potency, do not produce consistent titratable dosages and do not produce different remedies base on the "acids" (THCA/CBDA), the "neutrals" (THC/CBD) and the "analogs" (THCV/CBDV). In contrast, the preferred embodiment of the invention creates a higher potency tincture than any other in the market place today. According to the Tincture Potency Survey Fall of 2010, tinctures produced by this process are 10 times more potent than the average tincture. The process can create a variety of different remedies based on different cannabinoid ratios. For example, the process creates nine unique ratios between THCA/CBDA, THC/CBD and THCV/CBDV remedies. The process generates titratable dosages. This process produces dosages ranging from 2.5% mg/ml to 30% mg/ml. This is important because there is a minimum dosage (2.5 mg/ml), below which the medicinal value is not experienced, and a maximum dosage (30 mg/ml), above which the medicinal value is decreased (cannabinoids are Bi-Phase medicine).

DESCRIPTION

In one embodiment of the present disclosure, the extraction procedure and delivery approach are provided that allow selective utilization of various cannabinoid molecules from the whole cannabis sativa plant. These various cannabinoid compounds are designed to selectively affect various cannabinoid receptors in the nervous system, immune system and other tissues. In one aspect of at least one embodiment of the present disclosure, the extract is an oil-based whole plant product that contains all of the active compounds contained in the cannabis plant. In one embodiment of the present disclosure, the methods of obtaining the active compounds are explained in the "Procedure Methodology" section referenced below. In another aspect of at least one embodiment of the present disclosure, the whole cannabis plant product is then allowed to dry after one of the extraction methods described herein is performed. In yet another aspect of at least one embodiment of the present disclosure, one portion of the whole cannabis plant product is then heated while the other segment is left at room temperature. In yet another aspect of at least one embodiment, the heat-formulated (CEh) cannabis extract is kept separated from the cold-formulated (CEc) cannabis extract.

Figure 1:
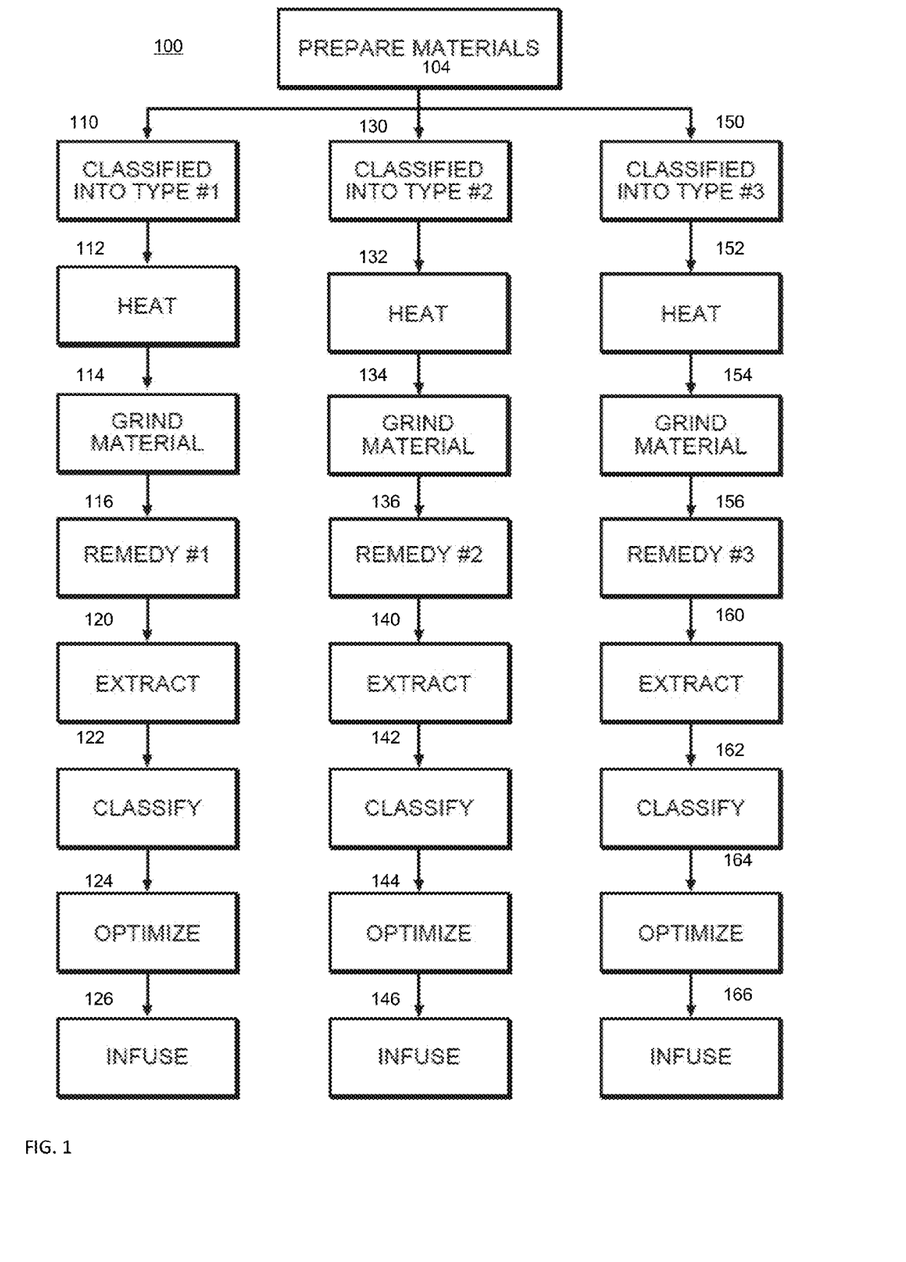
FIG. 1 shows an exemplary process for forming cannabis treatment compositions.

FIG. 1 shows an exemplary process 100 for forming cannabis treatment compositions. First, materials are prepared (104). This method starts with the naturally occurring phytocannabinoids of the cannabis plant. It utilizes home based extractors (reflux, ultrasonic etc.) to produce extracts that are unique combinations of medicinal phytocannabinoids (acids, neutrals and analogs) that enable Medical Cannabis Patients to titrate oral cannabis tinctures.

Next, the materials are classified into three types: type 1 (110), type 2 (130), and type 3 (150). In one embodiment, the process divides the Phytocannabinoids into three classes; acids, neutrals and analogs.

Type 1—Acids:
Delta 9 Tetrahydro-Cannabinol Acid (THCA) and Cannabidiol Acid (CBDA):
Method of Action=CB (1) and CB(2) brain receptors.

THCA

CBDA

Delta 9 Tetrahydro-Cannabinol Acid (THCA) is the most abundant cannabinoid main in the cannabis plant. THCA does not affect the Central Nervous System (CNS); it is not psycho active and it not used as recreational drug. Recent research confirms that THCA has anti-inflammation value it that it inhibits COX-1 and COX-2 enzymes (1).

THCA occurs in almost all Cannabis plants in concentrations that vary from traces to about 95 percent of all the phytocannabinoids in any plant sample. In very potent varieties, carefully prepared cannabis can have up to 30 percent delta-9 THCA by dry weight of the sample (seeds and stems removed from flowering buds).

Cannabidiol Acid (CBDA) is the second most abundant cannabinoid in the cannabis plant. CBDA occurs in almost all varieties. Concentration range from nil, to about 95 percent of the total cannabinoids CBDA does not affect the Central Nervous System (CNS), it is not psycho active, and it not used as recreational drug. Recent research confirms that THCA has anti-inflammation value it that it inhibits COX-1 and COX-2 enzymes. (1)

Type 2—Neutrals:
Delta 9 Tetrahydro-Cannabinol (THC) and Cannabidiol (CBD).

Method of Action=Inhibit COX-1 and COX-2 enzymes

Delta 9 Tetrahydro-Cannabinol (THC) is the most widely researched and widely used ingredient of cannabis. It affects the central nervous system via the CB-1 and CB-2 brain receptors. THC, in its natural form, is one of the safest therapeutically active substances known to man. THC can generate a euphoric experience and enhance creativity given the appropriate dosage, set and setting. THC has also been shown to enhance spiritual practices.

Cannabidiol (CBD) is the second most widely researched (2) and widely used ingredient of cannabis. It does effect the Central Nervous System directly via the CB(1) and CB(2) receptors and by interfering with the ability of THC to bind to the receptors.

CBD can increase alertness and prolong the effects of THC by decreasing the rate of THC clearance from the body, by interfering with the metabolism of THC in the liver. Medically, it has been shown to relieve convulsion, inflammation, anxiety, and nausea, and to inhibit cancer cell growth. Cannabidiol can be as effective as atypical antipsychotics in treating schizophrenia and ADHD.

When CBD and THC are taken together they interact and potentiate (enhance) or antagonize (interfere or lessen) certain medicinal qualities.

Type 3—Analogs:
Tetrahydrocannabivarin (THCV) and Cannabidivarine (CBDV)

Method of Action =CB(1) and CB(2) receptors

Tetrahydrocannabivarin (THCV) also known as tetrahydrocannabivarol, is a non-psychoactive cannabinoid found naturally in Cannabis. It is an analogue of tetrahydrocannabinol (THC). THCV has been shown to be a CB1 receptor antagonist, i.e. blocks the effects of THC.

Cannabidivarine (CBDV) also known as cannabidivarol, is a non-psychoactive cannabinoid found in the Cannabis plant. It is an analogue of cannabidiol (CBD), with the side-chain shortened by two CH2 groups This process is used with all Cannabis strains: Sativa, Indica, Ruderalis and all hybrids. Total plant material of Cannabis sativa has high levels of THCA and low levels of CBDA. Cannabis Indica has medium levels of THCA and medium levels of CBDA and high levels of THCV and CBDV. Cannabis Ruderalis has low levels of THCA and high levels of CBDA.

Next, elements (Steps) of the method are disclosed. First, the process prepares the Total Cannabis Plant Material (104). Implementations of this element include:

Drying:
The cannabis plant is dried thoroughly. Suspend the total plant upside down and air-dry. Drying is complete when the leaves next to the flowering tops are brittle. Depending upon the humidity and ambient temperature, this takes approximately 24 to 72 hours. The residual water content in this material is about 8-13 percent. Extraction will not be effective unless the plant is dry.

Sorting:
Separated flowers, leaves and the stalks. The seeds are removed prior to extraction. The remaining material is crumbled or broken and the stems cut short with scissors.

Grinding:
Grind the material to a medium power. It is easier to grind the chopped stems separately and then mix the powdered material before proceeding to use a grinder.

Next, the process classifies the plant material into 3 types (110, 130 and 150). The process classifies the total plant material according to THCA/CBDA, THC/CBD and THCV/CBDV percent of phytocannabinoids per gram of dry weight plant material. The THCA/CBDA, THC/CBD and THCV/CBDV % gram of plant material can be determined the following ways:

Analysis with a cannabinoid detection Kit
Analysis from a Laboratory using a Gas or Liquid Chromatograph
Strain Based estimate
Personal Experience
Other Knowing the % per gram of THCA/CBDA, THC/CBD and THCV/CBDV allows the user to use tables 1-3 for the Acids, (High/Low, Medium/Medium, Low/High) table 4-6 for the Neutrals (High/Low, Medium/Medium, Low/High) and tables 7-9 for the Analogs (High/Low, Medium/Medium, Low/High) to select the grams you will need to add to the solvent (base line 100 ml) in Step #4.

Next, the process heats the plant material (112, 132,152). This operation can skipped if the user does not want to activate the THC. To produce the acids one can skip this step because heating the plant material above 200 (f) converts the acids into the neutrals and or into the analogs. In order to maintain the acids form the user has to do a cold extraction. Reflux can be done under 200 (f) but it takes longer (2-4 hours), Ultrasonic extraction, takes 10 minutes and is done cold so it preserves the acid form.

To convert the acids (THCA/CBDA) to the neutrals (THC/CBD) and or the analogs (THCV/CBDV) the user can heat an oven to 220 F. To produce the neutrals and or the analogs the user heats to induce decarboxylation (11) which generates the following transformations: 1) THCA to THC, 2) CBDA into CBD, 3) CBDVA to CBDV and 4) THCVA into THCA (6). The cannabis is placed on a cookie sheet and placed in the oven for 60 minutes at 220 (f).

Next, the process selects the total plant material (grams) to solvent (milliliters) ratios and then grinds the materials (114, 134,154) and form remedies 1, 2 or 3 (116, 136, 156).

Based on the classification (cannabinoid potency) from step #2, select the grams of plant material that you will need to add to the solvent (base is 100 ml) in this step. The table will also specify the grams to milliliters (g/m) ratio. Select the potency of the remedy you desire (2.5% to 30% mg/ml), select the potency as specified in step #2, and to the right the table will tell you the grams of plant material you need to add to the solvent.

The higher the THC/CBD % per gram the less plant material per milliliter of solvent is required. The Tables (1-9) are based on the following formula for converting plant material (grams % of dry weight) into liquid extracts (milligrams per milliliters).

Convert % of gram dry weight plant material based on potency (Step #2) to milligrams per milliliter of tincture
1 gram=1 milliliter
10% of gram (g)=0.10 gram=100 mg's=100 mg/ml Example One gram of plant classified at 10% THC per gram=0.1 grams of THC or 100 milligrams
0.1 gram of THC (100 mg)=100 mg/ml

| Grams | 10% THC | MG's = ML |
|---|---|---|
| 1 | 10% | 100 = 100 mg/ml |

The user selects the material (grams) to solvent (milliliter) ratios for each remedy based on the cannabinoid (THCA/CBDA, THC/CBD and THCV/CBDV) % per gram of as determined in operations 110/130/150. This process assumes 100% extraction of the cannabinoids. Home reflux extractors using 190 proof alcohol solvent are 95%-99% efficient. Home ultrasonic extractors using 190 proof alcohol solvent are 97%-100% efficient. The potency, consistency and flavor of the tincture are a function of the plant material to solvent amounts in the tables listed below.

| Acids: | | |
|---|---|---|
| 1. Remedy #1: | Table 1 | High THCA/Low CBDA |
| 2. Remedy #2: | Table 2 | Medium THCA/Medium THCA |
| 3. Remedy #3: | Table 3 | Low THCA/High CBD |
| Neutrals: | | |
| 4. Remedy #4: | Table 4 | High THC/Low CBD |
| 5. Remedy #5: | Table 5 | Medium THC/Medium CBD |
| 6. Remedy #6: | Table 6 | Low THC/High CBD |
| Analogs: | | |
| 7. Remedy #7: | Table 7 | High THCV/Low CBDV |
| 8. Remedy #8: | Table 8 | Medium THCV/High CBDV |
| 9. Remedy #9: | Table 9 | Low THCV/High CBDV |

Next, the process performs cannabinoids extracting (120, 140 and 160). The cannabinoids (THCA/CBDA, THC/CBD and THCV/CBDV) are extracted from the cannabis material by refluxing (95% to 99% efficient) (9), and or ultrasonic extraction (95% to 99% efficient).

The extract, using reflux or ultrasonic extractors, the ground plant material in the selected plant material to solvent ratio (Table 1-9), in 190 proofs neutral grain spirits, for the appropriate time (that depends on the extraction apparatus being used) at a temperature between 140 (f) and 175 (f).

The present system and method create an organic cannabis based medicinal extract which includes how the "reflux" or "ultrasonic" extract processes are used. The process includes:
 a. Preparing the material (Step #1)
 b. Classifying the base material into specified cannabinoids categories according to their % cannabinoid content per gram of dry weight plant material (THCA/CDBA, THC/CBD and THCV/CBDV). (Step #2)
 c. Heating (before refluxing or using ultrasonic) at specific temperatures to induce the desired decarboxylation 1) THCA into THC, 2) CBDA into CBD, 3) THCVA into THCV and 4) CBDVA into CBDV. (Step #3).
 d. Selecting the Plant Material (grams) to Solvent (milliliter) amounts as specified in Table 1-9. (Step #4)
 e. Extracting in the specified gram to solvent amounts using home extractors to produce specified THCA/CBDA, THC/CBD and THCV and CBDV amounts in the remedies. (Step #5)
 f. Optimizing: increasing or decreasing potency (Step #6)
 g. Infusing with an alternative to alcohol (Step #7)

The process can classify the resulting products (122, 142, 162). The extracts can be optimized (124, 144,164). The potency can be increased by refluxing or evaporating to extract alcohol (use a collection vessel) to the desired potency or decrease the potency by adding alcohol to reach the desired potency. Remove the alcohol according to simple ratios. For example if the remedy is 10% potency and you want to increase to 15% (50% increase) reduce the alcohol by 50%, To increase the potency remove the alcohol according to the example above to achieve the desired potency. The alcohol can be reduced by refluxing with a collection vessel at 140 (f) to 175 (f). This will extract the alcohol by catching it in a container or heat tincture at a low temperature to evaporate the Alcohol to reach the desired potency. Make sure the temperature is below the boiling point (178 (f)) of Alcohol.
 To decrease the potency add alcohol or other alternative according reach the desired potency. For example, if the remedy is a 10% potency and you want to decrease it to 5% (50% decrease) increase the alcohol by 50%.

This operation is also optional and can be done if the user desires for the potency to be increased or decreased.

Next the resulting products undergo an infusing operation (126, 146,166). One embodiment creates an emulsion of an alternative to replace the Alcohol (i.e. Glycerin, Water. Stevia, Honey etc.). For each remedy, the user can reflux or evaporate the alcohol using a collection vessel to capture the alcohol according to the following specifications:

For each extract of Step #5, reduce alcohol by refluxing (12) to remove the solvent at a temperature (140-175 (f) below the boiling point of alcohol (178 (f)) to the level desired (10%-90%). Replace the alcohol that was removed with the alternative emulsion.

In sum, the system takes the initial plant material and produces nine distinct remedies:

| Acids: | | |
|---|---|---|
| 1. Remedy #1: | Table 1 | High THCA/Low CBDA |
| 2. Remedy #2: | Table 2 | Medium THCA/Medium THCA |
| 3. Remedy #3: | Table 3 | Low THCA/High CBD |
| Neutrals: | | |
| 4. Remedy #4: | Table 4 | High THC/Low CBD |
| 5. Remedy #5: | Table 5 | Medium THC/Medium CBD |
| 6. Remedy #6: | Table 6 | Low THC/High CBD |
| Analogs: | | |
| 7. Remedy #7: | Table 7 | High THCV/Low CBDV |
| 8. Remedy #8: | Table 8 | Medium THCV/High CBDV |
| 9. Remedy #9: | Table 9 | Low THCV/High CBDV |

The total plant material is dried, sorted and grinded. Then the plant material is classified according to cannabinoid (THCA/CBDA, THC/CBD, and THCV/CBDV) potency levels. If a user desires to produce a remedy with the neutrals and the analogs, the system heats the acid base plant material in the oven for 60 minutes at 220 (f). This step uses heat to induce decarboxylation which generates the following transformations: 1) THCA into THC, CBDA to CBD, THCVA to THCV and CBDVA to CBDV (12). Next, depending upon the test results, the system selects the plant material to solvent ratio using tables 1-3 for the acids (high/low, medium/medium. low/high) remedies, table 4-6 for the neutrals (high/low, medium/medium, low/high) and tables 7-9 for the analogs (high/low, medium/medium, low/high). The higher the cannabinoid content level, the lower the plant material per milliliter of solvent. Table 1-9 provide "grams to solvent" amounts for dosages ranging from 2.5% to 30%. The potency, consistency and flavor of the tincture are a function of the plant material to solvent amounts. The cannabinoids are extracted from the cannabis material by refluxing or ultrasonic extraction in 190 proof alcohols. Reflux the ground plant material using the selected plant material to solvent amounts in Tables 1-9, in 190 proofs neutral grain spirits, for the appropriate time and at the appropriate temperature (as specified below). This step extracts the cannabinoids into the alcohol. In optimization, if desired, the potency is increase by removing alcohol or decreased by adding alcohol or an alternative to alcohol (Glycerin, Water, Stevia). This is accomplished by capturing the alcohol in a collection vessel during the reflux process or by evaporating the alcohol. Next, the system creates an emulsion between Alcohol, Glycerin and Water according to the specifications and adds the appropriate amount of Glycerin to each remedy.

In one embodiment, an automated sorting device can be used. Various refluxing extractors from home versions to large industrial "reflux distillers" can be used. In one embodiment, an extractor from Eden Labs can be used. These distillation devices are "modified soxhlet extractors" where the modifications enable the operator to distill at much lower temperatures and it enables one to recollect the solvent that was used to extract the plant material back out of the extract for re-use. Within an enclosed flask there is an inverted condenser pointing down into the flask from the top. Just below that condenser will be suspended either what's called a soxhlet basket or a recovery vessel depending on whether the user is extracting or recovering solvent. The condenser will have cold liquid circulating through it to keep the condenser cold. In the bottom of the main flask solvent is placed. To do an extraction, the ground plant material is placed in the soxhlet basket which is a vessel with perforated sides and bottom so that liquid can fall through it. When gentle heat is applied to the main flask, the solvent begins to evaporate and the solvent vapors reach the cold condenser at the top of the flask and begin to liquefy on the sides of the condenser. (much the same way that a cold glass of water becomes wet on the outside of itself on a hot day) The re-condensed solvent on the sides of the condenser begin flowing down the sides of the condenser and begin dripping off of drip points on the end of the condenser. This solvent drips into the top of the soxhlet basket where it saturates the herb being extracted. The solvent flows through the basket and out the holes in the bottom of the basket carrying the extract with it into the bottom of the flask. The extract laden solvent falling from the soxhlet basket is dark in color and as it becomes clearer the plant material is leached out and the process is finished.

Alternatively, reflux can be used to extract the cannabis material. Reflux is a technique for involving the condensation of vapors and the return of a condensate to the system from which it originated. It is used in industrial and laboratory distillations. It is also used in chemistry to supply energy to reactions over a long period of time. A liquid reaction mixture is placed in a vessel open only at the top. This vessel is connected to a Liebig or Vigreux condenser, such that any vapors given off are cooled back to liquid, and fall back into the reaction vessel. The vessel is then heated vigorously for the course of the reaction. The purpose is to thermally accelerate the reaction by conducting it at an elevated temperature (i.e. the solvent's boiling point). The advantage of this technique is that it can be left for a long period of time without the need to add more solvent or fear of the reaction vessel boiling dry as any vapor is immediately condensed in the condenser. In addition, as a given solvent will always boil at a certain temperature, one can be sure that the reaction will proceed at a constant temperature. By careful choice of solvent, one can control the temperature within a very narrow range. The constant boiling action also serves to continuously mix the solution, although a magnetic stirring rod mechanism is often used to achieve a uniform solution. This technique is useful for performing chemical reactions under controlled conditions that require substantial time for completion. In one embodiment, a reflux apparatus for applying energy to chemical reactions includes an optional beaker of water between the reactants and the heat. This is often used as a safety precaution when using flammable reactants and a Bunsen burner in order to keep the flame away from the reactants. In modern laboratories, open flames are avoided due to the many flammable solvents often in use, and electrical heating, (i.e., with a hot plate or mantle) is preferred. Furthermore, a high boiling, thermally stable silicone oil is generally used to immerse the reaction vessel, rather than water which evaporates too readily to be useful for lengthy reactions. Using an oil bath, temperatures of up to several hundred degrees can easily be achieved, which is higher than the boiling point of most commonly used solvents. If even higher temperatures are required, the oil bath can be replaced with a sand bath.

Figure 2:
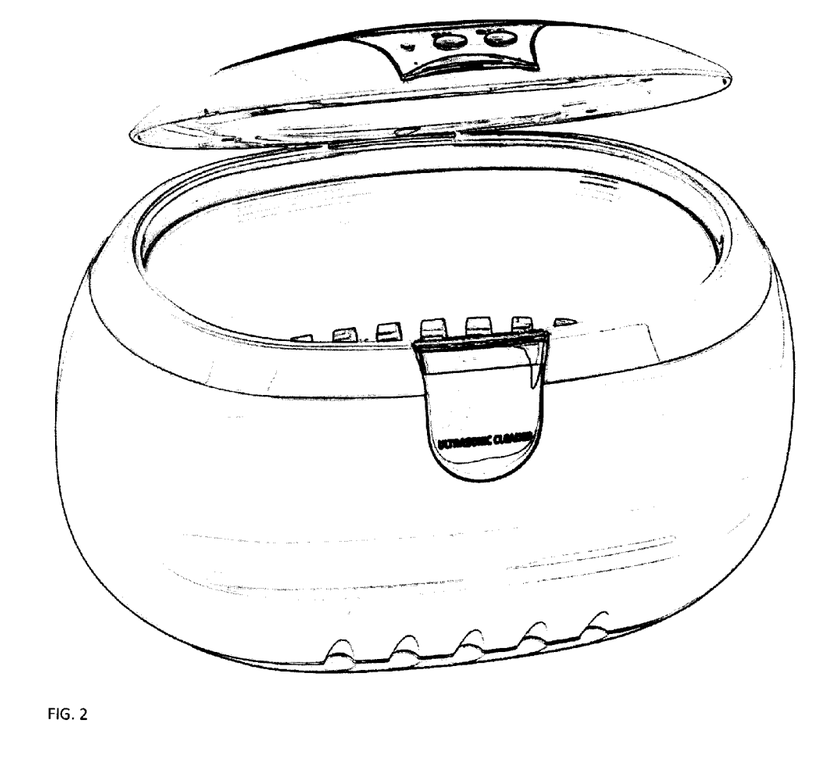
FIG. 2 shows an exemplary ultrasound extractor.

FIG. 2 shows an exemplary ultrasonic cleaner that uses about 42,000 cycles sonic energy waves to extract cannabis materials without heat or flammable solvents. The passage of ultrasonic waves through a liquid produces regions of compression and rarefaction. In the rarefaction regions, a "negative pressure" exists and the liquid is trying to tear itself apart. When it succeeds, it produces a cavity or bubble whose lifetime is extremely short. At the next region of compression, a small fraction of a second later, the cavity or bubble is squeezed, its walls are forced in upon the air or vapor it contains and the cavity or bubble may collapse. In that instant before the collapse, the pressure of gas or vapor within the cavity or bubble may reach several thousand times that of the atmosphere. When the cavity does collapse, it releases energy in the form of pressure and heat and powerful shock waves are formed. The formation of such bubbles in a liquid is called cavitation. Properly controlled, cavitation bubbles can be employed to knock unwanted softer material from harder surfaces One method of producing the ultrasonic waves is through the use of an electronic generator to supply electrical energy to a transducer. The transducer is mounted to a support structure which also houses and supports the electronic generator and the cleaning tank. The cleaning tank sits down and rests on the transducer and is supported by the support structure. A lid rests on the top or upper edge of the cleaning tank or on the edge of the support structure which surrounds the upper edge of the cleaning tank. Cleaning solution is introduced into the tank to the proper depth and the items to be cleaned are placed in the tank and the electronic generator is activated. The ultrasonic energy generating element, generally a piezoelectric actuator device, is energized for a large percentage of the time that the cleaner is in operation. This ultrasonic cleaner is safe, gentle and thorough. The ultrasonic extractor, along with the processes disclosed herein, generates titratable dosages. This process produces dosages ranging from 2.5% mg/ml to 30% mg/ml. This is important because there is a minimum dosage (2.5 mg/ml), below which the medicinal value is not experienced, and a maximum dosage (30 mg/ml), above which the medicinal value is decreased. Cannabinoids are Bi-Phase medicines.

Figure 3:
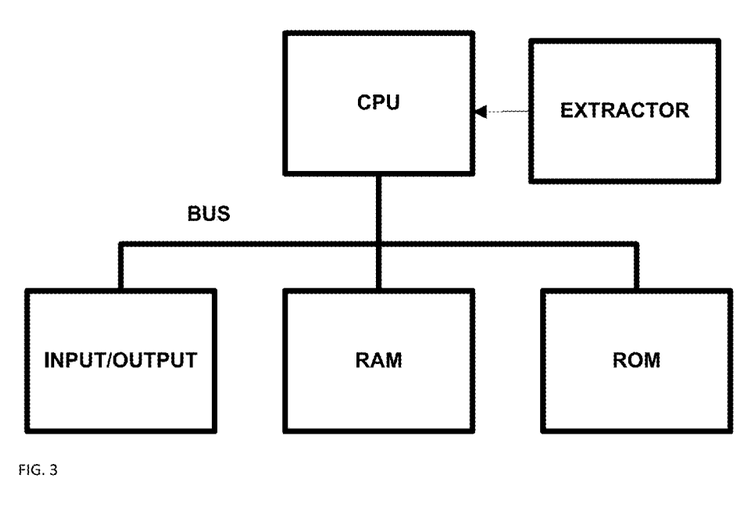
FIG. 3 shows an exemplary a processor controlled system for forming cannabis treatment.

The preparation process of FIG. 1 can be automated using the ultrasound extractor of FIG. 2 and a processor controlled system as shown in FIG. 3. The computer of FIG. 3 can be an embedded low power processor from ARM or Microchips, among others. The system employs organic material (total cannabis plant material and neutral grape spirits 190 proof ethanol) and organic processes (refluxing or ultrasonic wave) without chemical additives.

The computer of FIG. 3 can control a dryer to dry a cannabis plant material; means for classifying the cannabis plant material into an acid, neutral, or analog form; a grinder to grind the cannabis plant material. The processor can execute computer readable code to select a plant material to solvent amounts using a predetermined ratio. An extractor can be coupled to the processor, the extractor selected from a group including a reflux machine for evaporating and condensing the cannabis plant material or an ultrasonic extractor to extract cannabinoids from the cannabis plant material with ultrasonic waves; wherein the processor controls the extractor to extract in a predetermined materials to solvent amount required to produce a specified THCA/CBDA, THC/CBD and THCV and CBDV amount for use in one or more remedies; and wherein the processor controls the extractor to infuse the cannabinoids with an alternative emulsion. The extractor can be controlled to produce high potency tinctures of cannabinoids in three forms: 1) cannabinoid acids: THCA and CBDA, 2) cannabinoid neutrals: THC and CBD and 3) cannabinoid "analogs" THCV and CBDV. The computer code can provide users with options for producing cannabinoids ratio remedies of acid, neutral and analog forms in high/low, medium/medium and low/high ratios:

1. High THCA/Low CBDA,
2. Medium THCA/Low CBDA,
3. Low THCA/High CBDA
4. High THC/Low CBD
5. Medium THC/Medium CBD,
6. Low THC/High CBD
7. High THCV/Low CBDV,
8. Medium THCV/Medium CBDV
9. Low THCV/High CBDV.

The invention may be implemented in hardware, firmware or software, or a combination of the three. Preferably the invention is implemented in a computer program executed on a programmable computer having a processor, a data storage system, volatile and non-volatile memory and/or storage elements, at least one input device and at least one output device.

By way of example, a block diagram of a computer to support the system is discussed next. The computer preferably includes a processor, random access memory (RAM), a program memory (preferably a writable read-only memory (ROM) such as a flash ROM) and an input/output (I/O) controller coupled by a CPU bus. The computer may optionally include a hard drive controller which is coupled to a hard disk and CPU bus. Hard disk may be used for storing application programs, such as the present invention, and data. Alternatively, application programs may be stored in RAM or ROM. I/O controller is coupled by means of an I/O bus to an I/O interface. I/O interface receives and transmits data in analog or digital form over communication links such as a serial link, local area network, wireless link, and parallel link. Optionally, a display, a keyboard and a pointing device (mouse) may also be connected to I/O bus. Alternatively, separate connections (separate buses) may be used for I/O interface, display, keyboard and pointing device. Programmable processing system may be preprogrammed or it may be programmed (and reprogrammed) by downloading a program from another source (e.g., a floppy disk, CD-ROM, or another computer).

Each computer program is tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

The invention has been described herein in considerable detail in order to comply with the patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself. Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention. The following claims are intended to encompass all such modifications.

What is claimed is:

1. A method for producing a medicine from a cannabis plant consisting essentially of extracting cannabinoids from the cannabis plant by either a reflux process through evaporating and condensing the cannabis plant or an ultrasonic extraction process of the cannabis plant with ultrasonic waves to produce refluxed or extracted cannabinoids, and then infusing the refluxed or extracted cannabinoids with glycerine or honey to produce the medicine from a cannabis plant.

2. The method of claim 1 wherein the cannabinoids are in a form selected from the group consisting of acid, neutral and analog.

3. The method of claim 1 wherein the cannabinoids are selected from the group consisting of Tetrahydrocannabinol acid, cannabidiol acid, tetrahydro cannabinol, cannabidiol, tetrahydrocannabivarin, and cannabidivarine.

4. The method of claim 1 wherein the medicine has a water content less than 14% by weight of the total medicine.

5. A method for producing a medicine from a cannabis plant consisting essentially of extracting cannabinoids from the cannabis plant by either a reflux process through evaporating, heating and condensing the cannabis plant or an ultrasonic extraction process of the cannabis plant with ultrasonic waves and heat to produce refluxed or extracted cannabinoids, and then infusing the refluxed or extracted cannabinoids with glycerine or honey to produce the medicine from a cannabis plant.

6. The method of claim 5 wherein the cannabinoids are in a form selected from the group consisting of acid, neutral and analog.

7. The method of claim 5 wherein the cannabinoids are selected from the group consisting of Tetrahydrocannabinol acid, cannabidiol acid, tetrahydro cannabinol, cannabidiol, tetrahydrocannabivarin, and cannabidivarine.

8. The method of claim 5 wherein the medicine has a water content less than 14% by weight of the total medicine.

* * * * *